US010927467B2

(12) United States Patent
Lin

(10) Patent No.: US 10,927,467 B2
(45) Date of Patent: Feb. 23, 2021

(54) GAS GENERATOR

(71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 226 days.

(21) Appl. No.: 15/910,435

(22) Filed: Mar. 2, 2018

(65) Prior Publication Data

US 2018/0251904 A1  Sep. 6, 2018

(30) Foreign Application Priority Data

Mar. 3, 2017  (CN) .......................... 201710123059.3

(51) Int. Cl.
*C25B 9/00* (2021.01)
*C25B 15/08* (2006.01)
*C25B 1/04* (2021.01)
*A61M 16/10* (2006.01)
*C25B 9/08* (2006.01)

(52) U.S. Cl.
CPC ........... *C25B 15/08* (2013.01); *A61M 16/101* (2014.02); *C25B 1/04* (2013.01); *C25B 9/08* (2013.01); *A61M 2202/0208* (2013.01); *Y02E 60/36* (2013.01)

(58) Field of Classification Search
CPC .. C25B 15/08; C25B 1/04; C25B 9/00; C25B 1/02; C25B 9/06; C25B 15/00; C25B 15/02; C25B 1/00
See application file for complete search history.

(56) References Cited

U.S. PATENT DOCUMENTS

2005/0000802 A1* 1/2005 Hobbs ................. F17C 9/04
                                                      204/277
2014/0378745 A1* 12/2014 Lin ...................... C25B 9/06
                                                      600/27

FOREIGN PATENT DOCUMENTS

| CN | 100998535 A | 7/2007 |
| CN | 103785091 A | 5/2014 |
| CN | 205626644 U | 10/2016 |
| CN | 107773829 A | 3/2018 |
| GB | 2374021 A | 10/2002 |
| TW | 200817096 | 4/2008 |

* cited by examiner

*Primary Examiner* — Zulmariam Mendez

(57) ABSTRACT

The present invention provides a gas generator comprising an electrolytic device, a mixing chamber, and an atomizing chamber. The electrolytic device is configured for electrolyzing electrolyzed water to generate a gas with hydrogen. The mixing chamber is coupled to the electrolytic device for receiving the gas with hydrogen and mixing the gas with hydrogen with an atomized gas to generate a healthy gas. The atomizing chamber is coupled to the mixing chamber for generating the atomized gas. Wherein the maximum bore diameter of the mixing chamber is smaller than the maximum bore diameter of the atomizing chamber. The invention can reduce the possibility of the gas explosion by using the smaller volume of the mixing chamber and setting the anti-static device, since the smaller capacity of the mixing chamber has less hydrogen inside and the anti-static device is configured for reducing or eliminating the static electricity in the gas generator.

20 Claims, 4 Drawing Sheets

GAS GENERATOR

CROSS-REFERENCE TO RELATED APPLICATIONS

This application claims the priority benefit of Chinese Application Serial No. 201710123059.3 filed Mar. 3, 2017 the disclosure of which is incorporated herein by reference.

BACKGROUND OF THE INVENTION

1. Field of the Invention

The present invention relates to a gas generator, and more particularly, to a gas generator comprising the atomizing chamber with the maximum bore size larger than the maximum bore size of the mixing reaction chamber.

2. Description of the Prior Art

As people have always been paying much attention on health developments, many developments in medical technology are often targeted on treating diseases and prolonging human life. Most of the treatments in the past are passive, which means that the disease is treated only when it occurs. The treatments include an operation, a medication treatment, a radiation therapy, or even a medical treatment for cancer. However, in recent years, most of the researches from medical experts are gradually moving towards preventive medical methods, such as research on healthy food, screening and the prevention of inherited diseases, which actively prevents diseases from occurring in the future. Due to the focus of the prolongation of human life, many anti-aging and anti-oxidation technologies including skin care products and anti-oxidation food/medicine are gradually being developed and have become increasingly popular to the general public.

Studies have found that there are instable oxygen species ($O^+$), also known as free radicals, in the human body. The free radicals which are usually generated due to diseases, diet, environment and one's lifestyle can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage, but the lung damage could be ameliorated by inhaling hydrogen.

However, the gas with hydrogen generated by the electrolytic device is probably flammable if the hydrogen concentration is high enough. Even an electrostatic spark is likely to cause gas explosion. Therefore, the crisis of using electrolytic device is existed in prior art.

SUMMARY OF THE INVENTION

The present invention is to provide a gas generator for electrolyzing water to generate gas with hydrogen. Then the gas generator mixes the gas with hydrogen with atomized gas into healthy gas for inhaling. Besides, an accommodated space for accommodating the gas with hydrogen is minimized and combined with an anti-static device to reduce the possibility of explosion.

The gas generator of the present invention comprises an electrolytic device, a mixing reaction chamber, and an atomizing chamber. The electrolytic device accommodates the electrolyzed water containing an electrolyte. The electrolytic device is configured for electrolyzing the electrolyzed water to generate the gas with hydrogen. The mixing reaction chamber is coupled to the electrolytic device, and the mixing chamber is configured for receiving the gas with hydrogen and mixing the atomized gas with the gas with hydrogen to generate the healthy gas. The atomizing chamber is coupled to the mixing reaction chamber, and the atomizing chamber is configured for generating the atomized gas and transferring the atomized gas to the mixing reaction chamber. Wherein the maximum bore size of the mixing reaction chamber is smaller than the maximum bore size of the atomizing chamber.

In an embodiment, the volume of the mixing reaction chamber is less than the volume of the atomizing chamber.

In an embodiment, the gas generator further comprises an anti-static device set in the gas generator. The anti-static device is configured for reducing or eliminating the static electricity in the gas generator.

In another embodiment, the anti-static device is integrally formed in the gas generator.

In another embodiment, the anti-static device has a conductive end accommodated in the mixing reaction chamber.

In another embodiment, the mixing reaction chamber has an inner wall for accommodating the gas with hydrogen, the atomized gas, or the healthy gas, and the inner wall comprises the anti-static device.

In another embodiment, the anti-static device is configured in a place of the gas generator. The atomized gas, the gas with hydrogen or the healthy gas flows through the place of the gas generator.

In another embodiment, the anti-static device is coupled to a channel of the gas generator through which the atomized gas, the gas with hydrogen or the healthy gas flows.

In another embodiment, the flow direction of the atomized gas, the gas with hydrogen, or the healthy gas is perpendicular to a surface of the anti-static device.

In another embodiment, the anti-static device is configured within the gas generator in a replaceable manner.

In another embodiment, the anti-static device is removably configured within the gas generator.

In another embodiment, the mixing reaction chamber and the atomizing chamber are integrally formed.

In another embodiment, the mixing reaction chamber and the atomizing chamber are formed by injection molding.

In another embodiment, the mixing reaction chamber comprises a screw thread and the atomizing chamber comprises a corresponding screw thread, and the mixing reaction chamber and the atomizing chamber are combined through the screw thread and the corresponding screw thread.

In another embodiment, the gas generator further comprises a flame arrester configured in a channel of the gas generator through which the atomized gas, the gas with hydrogen or the healthy gas flows.

Another aspect of the present invention is to provide a gas generator comprising the electrolytic device, a mixing reaction chamber, and an atomizing chamber. The electrolytic device accommodates the electrolyzed water containing an electrolyte. The electrolytic device is configured for electrolyzing the electrolyzed water to generate the gas with hydrogen. The mixing reaction chamber is coupled to the electrolytic device, and the mixing chamber is configured for receiving the gas with hydrogen to mix the atomized gas with the gas with hydrogen to generate the healthy gas. The atomizing chamber is coupled to the mixing reaction chamber, and the atomizing chamber is configured for generating the atomized gas and transferring the atomized gas to the mixing reaction chamber. Wherein the mixing reaction chamber comprises a first shrunk section extended from the atomizing chamber.

In another embodiment, the volume of the mixing reaction chamber is less than the volume of the atomizing chamber.

In another embodiment, the mixing reaction chamber and the atomizing chamber are formed by injection molding.

In another embodiment, the mixing reaction chamber comprises a screw thread and the atomizing chamber comprises a corresponding screw thread, and the mixing reaction chamber and the atomizing chamber are combined through the screw thread and the corresponding screw thread.

In another embodiment, the gas generator further comprises an anti-static device set in the gas generator; the anti-static device is configured for reducing or eliminating the static electricity in the gas generator.

In another embodiment, the anti-static device is integrally formed in the gas generator.

In another embodiment, the anti-static device is coupled to a channel of the gas generator through which the atomized gas, the gas with hydrogen or the healthy gas flows.

To summarize, the objective of the present invention to provide a gas generator comprising the electrolytic device, a mixing reaction chamber, and an atomizing chamber. The gas generator of the present invention mixes the gas with hydrogen with the atomized gas into a healthy gas for human to inhale. By using the smaller volume of the mixing reaction chamber, the volume of the gas with hydrogen in the gas generator is reduced. The anti-static device is provided in the gas generator for reducing or eliminating the static electricity in the gas generator. Therefore, the gas generator is prevented from exploding caused by the static electricity, and the possibility of explosion of the gas with hydrogen is reduced as well.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
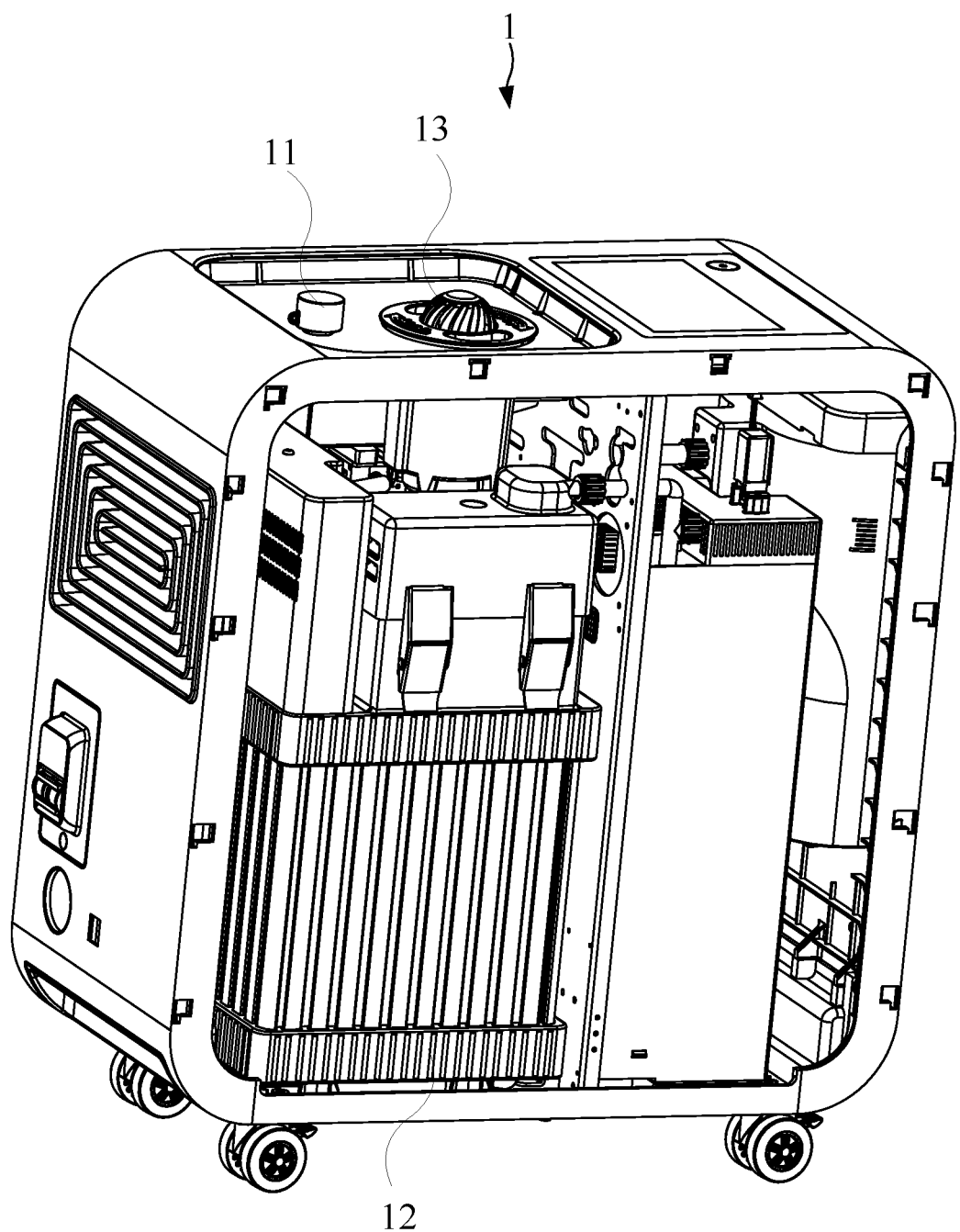
FIG. 1 and FIG. 2 show a schematic diagram of the gas generator with different visual angles in an embodiment of the present invention.
Figure 2:
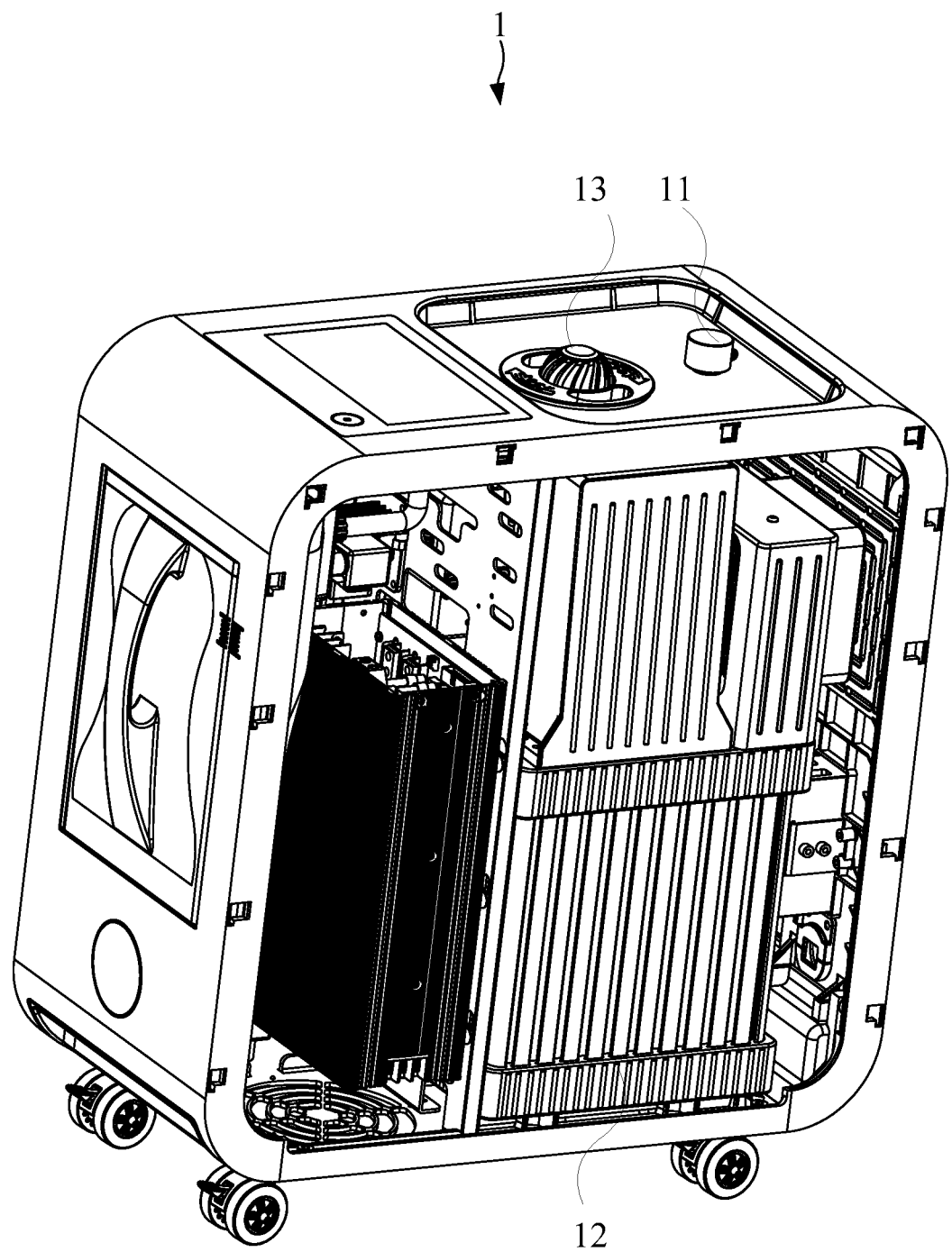
Figure 3:
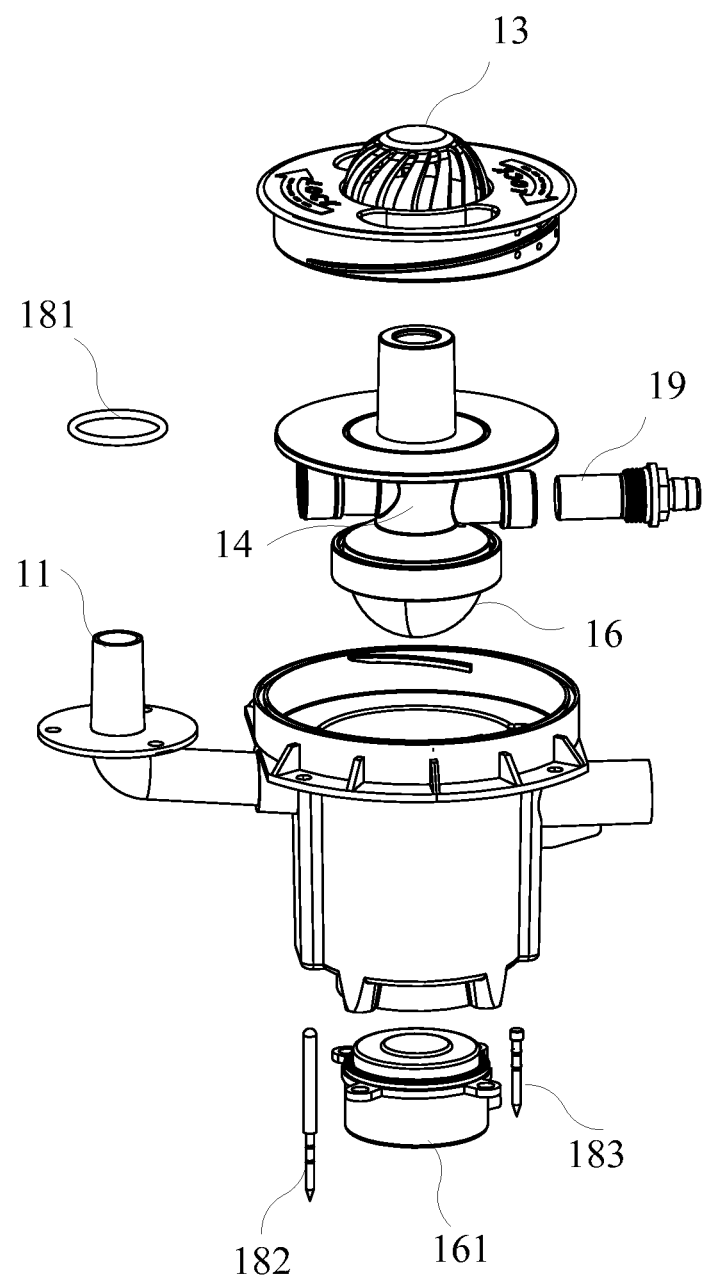
FIG. 3 illustrates a schematic diagram of mixing reaction chamber and atomizing chamber of the gas generator in an embodiment of the present invention.

Please refer to FIG. 1, FIG. 2, and FIG. 3. FIG. 1 and FIG. 2 show a schematic diagram of the gas generator 1 with different visual angles in an embodiment of the present invention. FIG.3 illustrates a schematic diagram of mixing reaction chamber 14 and atomizing chamber 16 of the gas generator 1 in an embodiment of the present invention. The gas generator 1 of the present invention comprises an electrolytic device 12, a mixing reaction chamber 14, and an atomizing chamber 16. The electrolytic device 12 accommodates the electrolyzed water comprising an electrolyte. The electrolytic device 12 is configured for electrolyzing the electrolyzed water to generate the gas with hydrogen. The mixing reaction chamber 14 is coupled to the electrolytic device 12, and the mixing reaction chamber 14 is configured for receiving the gas with hydrogen to mix the atomized gas with the gas with hydrogen to generate the healthy gas. The atomizing chamber 16 is coupled to the mixing reaction chamber 14, and the atomizing chamber 16 is configured for generating the atomized gas and transferring the atomized gas to the mixing reaction chamber 14.

Wherein the maximum bore size of the mixing reaction chamber 14 is smaller than the maximum bore size of the atomizing chamber 16.

In an embodiment, the volume of the mixing reaction chamber 14 is less than the volume of the atomizing chamber 16.

The gas generator 1 further comprises a draw tube 11 coupled to the mixing reaction chamber 14. The user may inhale the healthy gas, which is mixed within the mixing reaction chamber 14, via the draw tube 11 or directly inhale the non-mixed gas with hydrogen or the atomized gas. In an embodiment, the draw tube can further comprise a draw mask for the user to press close to the nose and mouth to inhale the healthy gas. Otherwise the gas generator 1 may further comprise a gas diffusion device allowing the gas to be more effectively inhaled by the user.

In an embodiment, the gas generator 1 further comprises an anti-static device disposed within the gas generator 1 for reducing or eliminating static electricity in the gas generator 1. In an embodiment, the anti-static device is a conductive conductor of a charge conductor, such as iron, copper, or gold foil, to balance the charge within the gas generator 1 to reduce or eliminate static electricity therein. In another embodiment, the anti-static device is a positive charge replenishing device or a negative charge replenishing device. The anti-static device eliminates the opposite charge in the gas generator 1 by means of charge replenishment. Therefore, the derived static electricity is reduced or eliminated.

According to another embodiment, the anti-static device has a conductive end configured within the mixing reaction chamber 14. In an embodiment, the anti-static device has a conductive end and a ground terminal. The ground terminal is coupled to the ground for balancing the potential in the ambient environment, thereby avoiding the accumulation of electric charge on the conductive end. Since the gas with hydrogen in the gas generator 1 is more likely to ignite than the atomized gas, the conductive end can be provided within the mixing reaction chamber 14, where the gas with hydrogen passes through. In an embodiment, the conductive end may be provided within the electrolytic device 12, or within a place the gas with hydrogen flows between the electrolytic device 12 and the suction tube 11. In another embodiment, a place of the gas generator 1 allows the atomized gas, the gas with hydrogen or the healthy gas to flow through, and the conductive end could be configured in the place of the gas generator 1. It also means the conductive end could be configured in where the atomized gas, the gas with hydrogen or the healthy gas flows through.

In another embodiment, the anti-static device is coupled to a channel of the gas generator 1 through which the atomized gas, the gas with hydrogen or the healthy gas flows. The channel can be a gas tube between each device or a flowing pathway in the device, even a tube connected to the external. The channel can be a place where the atomized gas, the gas with hydrogen or the healthy gas flows. In another embodiment, due to the possible heat source and leakage risk of circuit boards, the conductive end may be configured at any channel where the leakage may be happened or the electrostatic reaction may be occurred.

In an embodiment, the anti-static device is integrally formed in the gas generator 1. Since the anti-static device is an integrally formed metal conductive sheet, the gas generator 1 and the external environment come up to potential balance by a metal conductive sheet without splice. The accumulation of electrostatic due to the charge-transfer failure is thereby avoided.

In another embodiment, the anti-static device may be formed with other devices. In practice, the electrolytic device 12, the mixing reaction chamber 14 or the atomizing chamber 16 may be formed by injection molding or die casting. Within the manufacturing process, the anti-static device may be preliminarily provided in the place, such as the electrolytic device 12, the mixing reaction chamber 14 or the atomizing chamber 16, where the gas may flow through. The electrolytic device 12, the mixing reaction chamber 14 or the atomizing chamber 16 is cast or injection-molded with the anti-static device. Therefore, the electrolytic device 12, the mixing reaction chamber 14, and the atomizing chamber 16 have a better sealing effect. And the anti-static device retains the exposed surface to eliminate the static electricity. Furthermore, the anti-static device electrolytic device is fixed and the flow of gas is not blocked. Also, the difficulty of assembling and splicing will be solved.

In an embodiment, the mixing reaction chamber 14 has an inner wall for accommodating the gas with hydrogen, the atomized gas, or the healthy gas. The inner wall comprises the anti-static device. In an embodiment, the anti-static device may be a metal patch filled within the cavity of the entire mixing reaction chamber 14 in an attached way to form the inner wall. In another embodiment, the anti-static device is a metal container and is configured as the inner wall of the mixing reaction chamber 14.

The anti-static device is configured in a place of the gas generator 1, and the atomized gas, the gas with hydrogen or the healthy gas flows through the place of the gas generator 1. In practice, the gas generator 1 can further comprises a cooling device, a condensing device, a filter device, a wetting device, a sterilization device, and a gas pathway. The cooling device is configured for cooling down the gas or device. The condensing device is for condensing the gas with hydrogen to reduce the electrolyte, electrolyzed water, or steam. The filter device is configured for filtering the gas again. The wetting device is for wetting and purifying the gas. The sterilization device is configured for sterilizing. The gas pathway is for connecting each device mentioned above. The anti-static device can be configured in any device or pathway mentioned above in the gas generator 1. Therefore, the atomized gas, the gas with hydrogen or the healthy gas may flow through the anti-static device in the gas generator 1.

According to another embodiment, the anti-static device is perpendicular to the flowing direction of the atomized gas, the gas with hydrogen, or the healthy gas. The flow direction of the atomized gas, the gas with hydrogen, or the healthy gas is perpendicular to a surface of the anti-static device. Since the gas generator 1 contains flowing and continuously generated gas, the anti-static device perpendicular to the flowing direction is configured for contacting with different gas molecules, and the electrostatic generated in the gas generator 1 can be prevented. Further, the anti-static device may be a metal filter provided in gas inlet and gas outlet of each device thereby to ensure that the gas in each device is flowing through the anti-static device. In an embodiment, in order to evaluate the ease of installation, an anti-static device having a vertical structure may be provided at the inner surface of any device where the gas flows through in the gas generator 1. Therefore, the anti-static device contacts with different gas molecules while maintaining the ease of installation.

Please refer to FIG. 3. In an embodiment, the anti-static device is configured within the gas generator 1 in a replaceable manner. The anti-static device is removably configured within the gas generator 1. The anti-static device may be a conductive ring 181, a conductive pin 182 or a metal screw 183 for locking. The gas generator 1 further comprises a grounding wire for grounding to balance the charge of the above elements. According to the different device structures, the different anti-static device types are provided to match.

In practice, the anti-static device can be a material capable of transferring charge such as a metal mesh, a metal sheet or a metal film. Otherwise the anti-static device may be a conductive fixing element such as a screw, a wire or a spacer. At the same time, the anti-static device can be partially or completely disposed at the before-mentioned position, and the anti-static device can be completely filled or partially disposed in the preset device.

In another embodiment, the anti-static device can be a metal clip placed in a gas contact surface of the removable mixing reaction chamber 14 and the atomizing chamber 16. The anti-static device is fixed in a conductive shell; thereby the relative position of the mixing reaction chamber 14, the atomizing chamber 16, and the other devices is fixed while balancing the charge distribution of the passing gas.

In another embodiment, the anti-static device may even be a metal film. The anti-static device is smeared at the gas pathway of the gas generator 1 to balance the charge distribution of the gas contained within the gas generator 1. Therefore, the static is reduced and eliminated in the gas generator 1.

Furthermore, the electrolytic device 12 comprises a gas storage portion accommodating the gas with hydrogen, and the anti-static device is configured in the gas storage portion. The gas storage portion described herein has to be placed in where the gas with hydrogen electrolyzed by the electrolytic device 12 flows through.

Figure 4:
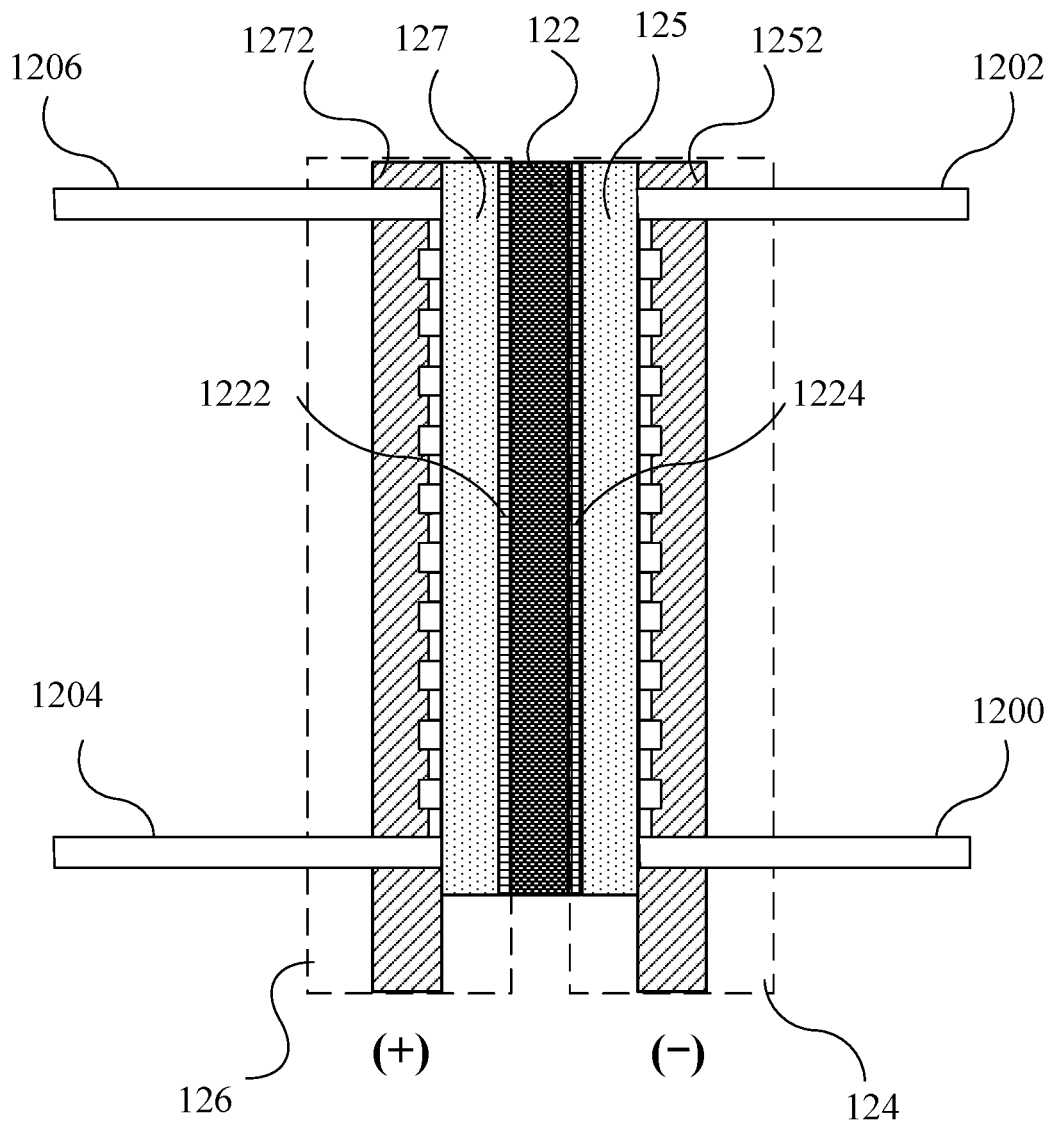
FIG. 4 illustrates a schematic diagram of ion membrane electrolytic device of the gas generator in an embodiment of the present invention.

Please refer to FIG. 4. FIG.4 illustrates a schematic diagram of ion membrane electrolytic device of the gas generator 1 in an embodiment of the present invention. In an embodiment, the electrolytic device 12 comprises an ion membrane electrolytic device, and the ion membrane electrolytic device comprises an ion exchange membrane 122, a cathode chamber 124 and an anode chamber 126. The cathode electrode 125 is set in the cathode chamber 124 and the anode electrode 127 is set in the anode chamber 126 as shown in FIG. 4 (the anode chamber 126 and the cathode chamber 124 are indicated by a dotted line). The ion exchange membrane 122 is set between the anode chamber 126 and the cathode chamber 124. Oxygen is generated by the anode electrode 127 and hydrogen is generated by the cathode electrode 125 while the ion membrane electrolytic device electrolyzes water. In an embodiment, water is contained in the anode chamber 126. The water in the anode chamber 126 may further penetrate into the cathode chamber 124 through the ion exchange membrane 122. In another embodiment, the anode chamber 126 and the cathode chamber 124 can accommodate water at the same time. The anode electrode 127 can electrolyze water to generate hydrogen ion and oxygen. The hydrogen ion can penetrate through the ion exchange membrane 122 to the cathode chamber 124, and hydrogen is generated on the cathode electrode 125 while getting the electrode. In practice, hydrogen can be generated, but not limited to, on the catalyst layer; hydrogen can also be generated on the electrode plate or between the ion membrane and the electrode plate.

Besides, the ion membrane electrolytic device comprises a cathode current-conducting plate 1252 and an anode current-conducting plate 1272. The cathode current-conducting plate 1252 is configured for connecting the external power supply and the cathode electrode 125. The anode current-conducting plate 1272 is configured for connecting the external power supply and the anode electrode 127. Furthermore, the ion membrane electrolytic device can further comprise a gas tube 1200, and the gas tube 1200 can connect the cathode chamber 124 and the outside. The ion membrane electrolytic device can further comprise the hydrogen tube 1202 coupled to the cathode chamber 124 to transfer the gas with hydrogen into the gas pathway. The ion membrane electrolytic device can further comprise a water supply tube 1204 to recharge water from the electrolytic device 12 into the cathode chamber 124 and the anode chamber 126. The ion membrane electrolytic device can further comprise an oxygen tube 1206 coupled with the anode chamber 126 to output oxygen to the outside from the electrolytic device 12. Besides, the ion membrane electrolytic device can further comprise a ratio regulator (not shown) coupled to the hydrogen tube 1202 and the gas pathway, further coupled to the gas tube 1200 or the oxygen tube 1206. Thereby the hydrogen concentration is regulated to generate the required gas with hydrogen and then the gas with hydrogen is transferred to the gas pathway.

In practical application, the ion exchange membrane 122 further comprises an anode catalyst layer 1222 and a cathode catalyst layer 1224. The anode catalyst layer 1222 can be selected from a group consisting of Pt, Ir, Pd, the alloy powder of Pt, carbon, or any combination thereof. The cathode catalyst layer 1224 can be selected from a group consisting of Pt, Ir, Pd, the alloy powder of Pt, or any combination thereof. In an embodiment, the material of the anode catalyst layer 1222 or the cathode catalyst layer 1224 can be configured into slurry to be coated on both sides of the ion membrane to form the anode catalyst layer 1222 and the cathode catalyst layer 1224.

Please refer to FIG. 3 again. According to another embodiment, the mixing reaction chamber 14 and the atomizing chamber 16 are formed together in the gas generator 1 in an integral manner. Further, the mixing reaction chamber 14 and the atomizing chamber 16 are formed together in an injection molding manner. Besides, the inner wall or the whole of the mixing reaction chamber 14 and the atomizing chamber 16 may be formed by the anti-static device for reducing or eliminating the static electricity. In another embodiment, the mixing reaction chamber 14 and the atomizing chamber 16 are formed respectively and then combined together. Furthermore, the mixing reaction chamber 14 and the atomizing chamber 16 are combined in a screw lock manner. In another embodiment, the mixing reaction chamber 14 comprises a screw thread and the atomizing chamber 16 comprises a corresponding screw thread, and the mixing reaction chamber 14 and the atomizing chamber 16 are combined through the screw thread and the corresponding screw thread.

In practice, the atomized gas system is derived from an atomized liquid, wherein the atomized liquid is selected from one of the groups consisting of water vapor, atomized solution, volatile essential oil and combinations thereof, and the atomized liquid is converted into the required atomized gas through a reformer. In an embodiment, the atomized liquid is pre-added and accommodated in the atomizing chamber 16. After that, the reformer (as shown in FIG. 4, an ultrasonic wave vibrator 161 located below the atomizing chamber 16) adjacent to the atomizing chamber 16 converting the atomized liquid to the required atomized gas. The reformer may be the vibrator 161 or a heater. If the reformer is a heater, highly volatile liquid with high vapor pressure characteristic can be configured as the atomized liquid. In an embodiment, since the atomized gas is converted from the atomized liquid by the reformer, the conversion efficiency is proportional to the reaction area of the reformer and the atomized liquid. Therefore, the reaction area between the reformer area and the atomized liquid is larger, the efficiency is higher. In another embodiment, the volume of the atomizing chamber 16 is increased in order to increase the atomization efficiency. The mixing reaction chamber 14 accommodates highly ignitable hydrogen; the volume of the mixing reaction chamber 14 affects the conversion efficiency of the atomized gas less. Thereby, if the volume of the mixing reaction chamber 14 is smaller than the volume of the atomizing chamber 16, the possibility of gas ignition is reduced, but the reaction efficiency thereof is maintained.

According to another embodiment, the gas generator 1 further comprises a flame arrester 19 configured in a place of the gas generator 1, and the atomized gas, the gas with hydrogen or the healthy gas flows through the place of the gas generator 1. In another embodiment, the flame arrester 19 configured in the channel of the gas generator 1 through which the atomized gas, the gas with hydrogen or the healthy gas flows. The flame arrester 19 can be configured at the inlet of the mixing reaction chamber 14. In order to avoid that electrostatic ignites atomized gas, the gas with hydrogen or healthy gas resulting in the chain of ignition or even gas explosion, a number of the flame arrester 19 can be provided within the gas pathway in the gas generator 1 to prevent the excessive damage.

In an embodiment, the internal parts of the gas generator 1 may be damaged by explosion and the plating solution exudation or the control circuit board damage may happened, the gas generator 1 further be provided with an explosion-proof hole 13. The explosion-proof hole 13 may be configured in where the atomized gas, hydrogen or the healthy gas flows through. Thereby a large amount of instantaneous gas can overflow from the explosion-proof hole 13. Wherein the explosion-proof hole 13 may be disposed above the mixing reaction chamber 14 and the explosion-proof hole 13 can be made of a soft silicone.

Another aspect of the present invention is to provide a gas generator 1 comprising the electrolytic device 12, a mixing reaction chamber 14, and an atomizing chamber 16. The electrolytic device 12 accommodates the electrolyzed water comprising an electrolyte. The electrolytic device 12 is configured for electrolyzing the electrolyzed water to generate the gas with hydrogen. The mixing reaction chamber 14 is coupled to the electrolytic device 12, and the mixing chamber 14 is configured for receiving the gas with hydrogen to mix the atomized gas with the gas with hydrogen to generate the healthy gas. The atomizing chamber 16 is coupled to the mixing reaction chamber 14, and the atomizing chamber 16 is configured for generating the atomized gas and transferring the atomized gas to the mixing reaction chamber 14. Wherein the mixing reaction chamber 14 comprises a first shrunk section extended from the atomizing chamber 16.

In an embodiment, a first diameter of the mixing reaction chamber 14 extends from the atomizing chamber 16 and is narrowed inward.

According to another embodiment, the volume of the mixing reaction chamber 14 is less than the volume of the atomizing chamber 16, thereby the gas generator 1 having the mixing reaction chamber 14 smaller than the atomizing chamber 16 is formed.

To summarize, the objective of the present invention to provide a gas generator comprising the electrolytic device, a mixing reaction chamber, and an atomizing chamber. The gas generator of the present invention mixes the gas with hydrogen with the atomized gas into a healthy gas for human to inhale. By using the smaller volume of the mixing reaction chamber, the volume of the gas with hydrogen in the gas generator is reduced. The anti-static device is provided in the gas generator for reducing or eliminating the static electricity in the gas generator. Therefore, the gas generator is prevented from exploding caused by the static electricity, and the possibility of explosion of the gas with hydrogen is reduced as well.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator, comprising:
    an electrolytic device for accommodating electrolyzed water, wherein the electrolytic device is configured for electrolyzing the electrolyzed water to generate gas with hydrogen;
    a mixing reaction chamber coupled to the electrolytic device, wherein the mixing reaction chamber is configured for receiving the gas with hydrogen and mixing the gas with hydrogen with atomized gas to generate healthy gas;
    a disc structure surrounding the mixing reaction chamber; and
    an atomizing chamber coupled to the mixing reaction chamber, wherein the atomizing chamber is configured to accommodate an atomized liquid for generating the atomized gas and transferring the atomized gas to the mixing reaction chamber;
    wherein the maximum bore size of the mixing reaction chamber is smaller than the maximum bore size of the atomizing chamber.

2. The gas generator of claim 1, further comprising an anti-static device set in the gas generator, wherein the anti-static device is configured for reducing or eliminating the static electricity in the gas generator.

3. The gas generator of claim 2, wherein the anti-static device is integrally formed in the gas generator.

4. The gas generator of claim 2, wherein the anti-static device has a conductive end accommodated in the mixing reaction chamber.

5. The gas generator of claim 2, wherein the mixing reaction chamber has an inner wall for accommodating the gas with hydrogen, the atomized gas, or the healthy gas, and the inner wall comprises the anti-static device.

6. The gas generator of claim 2, wherein the anti-static device is coupled to a channel of the gas generator through which the atomized gas, the gas with hydrogen or the healthy gas flows.

7. The gas generator of claim 6, wherein the flow direction of the atomized gas, the gas with hydrogen, or the healthy gas is perpendicular to a surface of the anti-static device.

8. The gas generator of claim 2, wherein the anti-static device is removably configured within the gas generator.

9. The gas generator of claim 1, further comprising a top cover and an accommodating chamber with an inner wall, wherein the atomizing chamber is positioned in the accommodating chamber, the disc structure is couple to the inner wall, and the top cover is vertically stacked above the mixing reaction chamber.

10. The gas generator of claim 1, wherein the mixing reaction chamber comprises two lateral protrusions protruding outward from opposite sides of the mixing reaction chamber, and one of the lateral protrusions is configured to receive the gas with hydrogen.

11. The gas generator of claim 1, further comprising a flame arrester configured in a channel of the gas generator through which the atomized gas, the gas with hydrogen or the healthy gas flows.

12. The gas generator of claim 1, wherein the volume of the mixing reaction chamber is less than the volume of the atomizing chamber.

13. The gas generator of claim 1, wherein the mixing reaction chamber comprises a screw thread and the atomizing chamber comprises a corresponding screw thread, and the mixing reaction chamber and the atomizing chamber are combined through the screw thread and the corresponding screw thread.

14. A gas generator, comprising:
    an electrolytic device for accommodating electrolyzed water, wherein the electrolytic device is configured for electrolyzing the electrolyzed water to generate gas with hydrogen;
    a mixing reaction chamber coupled to the electrolytic device, wherein the mixing reaction chamber is configured for receiving the gas with hydrogen and mixing the gas with hydrogen with atomized gas to generate the healthy gas; and
    an atomizing chamber coupled to the mixing reaction chamber, wherein the atomizing chamber is configured to accommodate an atomized liquid for generating the atomized gas and transferring the atomized gas to the mixing reaction chamber;
    wherein the mixing reaction chamber comprises a first shrunk section extended from the atomizing chamber, and the mixing reaction chamber further comprises two lateral protrusions protruding outward from the mixing reaction chamber, and one of the lateral protrusions is configured to receive the gas with hydrogen.

15. The gas generator of claim 14, wherein the volume of the mixing reaction chamber is less than the volume of the atomizing chamber.

16. The gas generator of claim 14, further comprises a disc structure surrounding the mixing reaction chamber.

17. The gas generator of claim 14, wherein the mixing reaction chamber comprises a screw thread and the atomizing chamber comprises a corresponding screw thread, and the mixing reaction chamber and the atomizing chamber are combined through the screw thread and the corresponding screw thread.

18. The gas generator of claim 14, further comprising an anti-static device set in the gas generator, wherein the anti-static device is configured for reducing or eliminating the static electricity in the gas generator.

19. The gas generator of claim 18, wherein the anti-static device is integrally formed in the gas generator.

20. The gas generator of claim 18, wherein the anti-static device is coupled to a channel of the gas generator through which the atomized gas, the gas with hydrogen or the healthy gas flows.

* * * * *